(12) United States Patent
Li et al.

(10) Patent No.: US 10,959,626 B2
(45) Date of Patent: Mar. 30, 2021

(54) SELF-POWERED WEARABLE FOR CONTINUOUS BIOMETRICS MONITORING

(71) Applicant: Samsung Electronics Co., Ltd., Suwon-si (KR)

(72) Inventors: Yelei Li, San Jose, CA (US); Matthew C. Wiggins, San Jose, CA (US)

(73) Assignee: Samsung Electronics Co., Ltd.

( * ) Notice: Subject to any disclaimer, the term of this patent is extended or adjusted under 35 U.S.C. 154(b) by 326 days.

(21) Appl. No.: 15/888,853

(22) Filed: Feb. 5, 2018

(65) Prior Publication Data

US 2019/0000332 A1    Jan. 3, 2019

Related U.S. Application Data

(60) Provisional application No. 62/587,351, filed on Nov. 16, 2017, provisional application No. 62/527,918, filed on Jun. 30, 2017.

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0006* (2013.01); *A61B 5/02427* (2013.01); *A61B 5/053* (2013.01); *A61B 5/681* (2013.01); *G01P 15/14* (2013.01); *H01M 10/465* (2013.01); *A61B 2560/0209* (2013.01); *A61B 2560/0214* (2013.01); *H01M 2/1066* (2013.01);
(Continued)

(58) Field of Classification Search
CPC ................ A61B 2560/0209; A61B 2560/0214
See application file for complete search history.

(56) References Cited

U.S. PATENT DOCUMENTS

| 9,724,042 | B1 * | 8/2017 | Lodato | A61B 5/02055 |
| 2015/0035378 | A1 * | 2/2015 | Calhoun | H02J 50/001 |
| | | | | 307/104 |

(Continued)

FOREIGN PATENT DOCUMENTS

| CN | 101232195 A | 7/2008 |
| CN | 101860262 A | 10/2010 |

(Continued)

OTHER PUBLICATIONS

U.S. Appl. No. 15/264,333, System and Method for Providing a Real-Time Signal Segmentation and Fiducial Points Alignment Framework, filed Sep. 13, 2016.

(Continued)

*Primary Examiner* — Michael W Kahelin
(74) *Attorney, Agent, or Firm* — Innovation Counsel LLP (57) ABSTRACT

A user-wearable device utilizes energy harvesting technology to lengthen battery life or eliminates the need to charge the wearable device. In one embodiment, a user-wearable device combines energy harvesting technology with low power sensors and high efficiency processing methods to realize a self-charging or battery-less biometric monitoring system. The wearable biometric monitoring system provides accurate biometric measurements while enhancing user experience by extending the battery life or completely eliminating the need for the user to charge the device.

12 Claims, 4 Drawing Sheets

(51) Int. Cl.
  *G01P 15/14*   (2013.01)
  *H01M 10/46*   (2006.01)
  *A61B 5/053*   (2021.01)
  *H01M 10/04*   (2006.01)
  *H01M 10/48*   (2006.01)
  *H01M 10/44*   (2006.01)
  *H01M 10/42*   (2006.01)
  *H01M 2/10*    (2006.01)

(52) U.S. Cl.
  CPC ...... *H01M 10/0436* (2013.01); *H01M 10/425* (2013.01); *H01M 10/44* (2013.01); *H01M 10/48* (2013.01); *H01M 2220/30* (2013.01); *Y02E 60/10* (2013.01)

(56) References Cited

U.S. PATENT DOCUMENTS

| | | |
|---|---|---|
| 2016/0015275 A1 | 1/2016 | Samadani et al. |
| 2016/0028264 A1 | 1/2016 | Bernhard |
| 2016/0220191 A1 | 8/2016 | Li et al. |
| 2016/0220192 A1 | 8/2016 | Wiggins et al. |
| 2017/0075426 A1 | 3/2017 | Camacho Perez et al. |
| 2017/0188847 A1 | 7/2017 | Ahmed et al. |
| 2017/0273635 A1 | 9/2017 | Li et al. |

FOREIGN PATENT DOCUMENTS

| | | |
|---|---|---|
| CN | 104622434 A | 5/2015 |
| CN | 104769766 A | 7/2015 |
| CN | 105549683 A | 5/2016 |
| KR | 10-2015-0048019 A | 5/2015 |
| WO | 2015058923 A1 | 4/2015 |

OTHER PUBLICATIONS

U.S. Appl. No. 15/370,468, System and Method for Snoring Detection Using Low Power Motion Sensor, filed Dec. 6, 2016.

U.S. Appl. No. 15/726,756, System and Method for Real-Time Heartbeat Events Detection Using Low-Power Motion Sensor, filed Oct. 6, 2017.

U.S. Appl. No. 15/726,827, System and Method for Continuous Background Heartrate and Heartbeat Events Detection Using a Motion Sensor, filed Oct. 6, 2017.

Office Action for Chinese Application No. 201810637344.1 dated Oct. 12, 2020, 12 Pages.

\* cited by examiner

SELF-POWERED WEARABLE FOR CONTINUOUS BIOMETRICS MONITORING

CROSS REFERENCE TO RELATED APPLICATIONS

This application claims priority to U.S. Provisional Patent Application No. 62/527,918, entitled SELF-POWERED WEARABLE DEVICE FOR CONTINUOUS BIOMETRICS MONITORING, filed Jun. 30, 2017, and also claims priority to U.S. Provisional Patent Application No. 62/587,351, entitled SELF-POWERED WEARABLE FOR CONTINUOUS BIOMETRICS MONITORING, filed Nov. 16, 2017, both of which are incorporated herein by reference for all purposes.

FIELD

The present disclosure relates generally to wearable devices and, in particular, to a self-powered wearable device for biometrics monitoring.

BACKGROUND

Wearable devices include a number of features and capabilities ranging from time tracking to providing health-related feedback. A wearable device typically provides basic functions such as telling the time and counting steps that require relatively little power. More advanced health functionality such as heartrate or heartbeat detection, sleep tracking, and blood pressure monitoring often have relatively high power requirements. Common techniques for making health measurements include using a photoplethysmogram (PPG), an electrocardiogram (ECG), an accelerometer and/or other sensors. A major complaint with the current generation of wearables is limited battery life and the need to charge the wearable devices. The battery life problem is compounded when users want continuous biometrics monitoring that can consume a large amount of power.

SUMMARY

The present disclosure discloses a device and method for self-powered or battery-less user-wearable device for biometric measurement, substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

In one embodiment, a user-wearable device for biometric measurement of a user includes an energy harvesting module configured to collect energy and to provide energy output; an energy storage module coupled to the energy harvesting module to store the energy output harvested by the energy harvesting module; a sensor module comprising a sensor and configured to measure at least one biological signal of the user and to process the biological signal using at least one biometric signal processing method where the sensor module is powered by the energy stored in the energy storage module; and a processor module configured to process the biological signal measured by the sensor by executing at least one power optimized biometric inference method on the biological signal where the processor module is powered by the energy stored in the energy storage module. The sum of the power consumed by sensing operation of the sensor module and signal processing operation of the processor module is at least partially supplied by the energy harvesting module, the sensor module and the processor module being controlled by an adaptive power control module configured to adjust a sensing a duty cycle schedule and a signal process time to realize power balance between the energy generation by the energy harvesting module and the energy consumption by the sensor module and the processor module.

BRIEF DESCRIPTION OF THE DRAWINGS

Various embodiments of the present disclosure are described in the following detailed description and the accompanying drawings.

DETAILED DESCRIPTION

The present disclosure can be implemented in numerous ways, including as a process; an apparatus; a system; a composition of matter; a computer program product embodied on a computer readable storage medium; and/or a processor, such as a hardware processor or a processor device configured to execute instructions stored on and/or provided by a memory coupled to the processor. In this specification, these implementations, or any other form that the disclosure may take, may be referred to as techniques. In general, the order of the steps of disclosed processes may be altered within the scope of the disclosure. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the disclosure is provided below along with accompanying figures that illustrate the principles of the disclosure. The disclosure is described in connection with such embodiments, but the disclosure is not limited to any embodiment. The scope of the disclosure is limited only by the claims and the disclosure encompasses numerous alternatives, modifications and equivalents. Numerous specific details are set forth in the following description in order to provide a thorough understanding of the disclosure. These details are provided for the purpose of example and the disclosure may be practiced according to the claims without some or all of these specific details. For the purpose of clarity, technical material that is known in the technical fields related to the disclosure has not been described in detail so that the disclosure is not unnecessarily obscured.

In embodiments of the present disclosure, a user-wearable device utilizes energy harvesting technology to lengthen battery life or to eliminate the need to charge the wearable device. In one embodiment, a user-wearable device combines energy harvesting technology with low power sensors and high efficiency biometric inference methods (or referred to as biometric signal processing methods) to realize a self-charging or battery-less biometric monitoring system. The wearable biometric monitoring system provides accurate biometric measurements while enhancing user experience by extending the battery life or completely eliminating the need for the user to charge the device.

Figure 1:
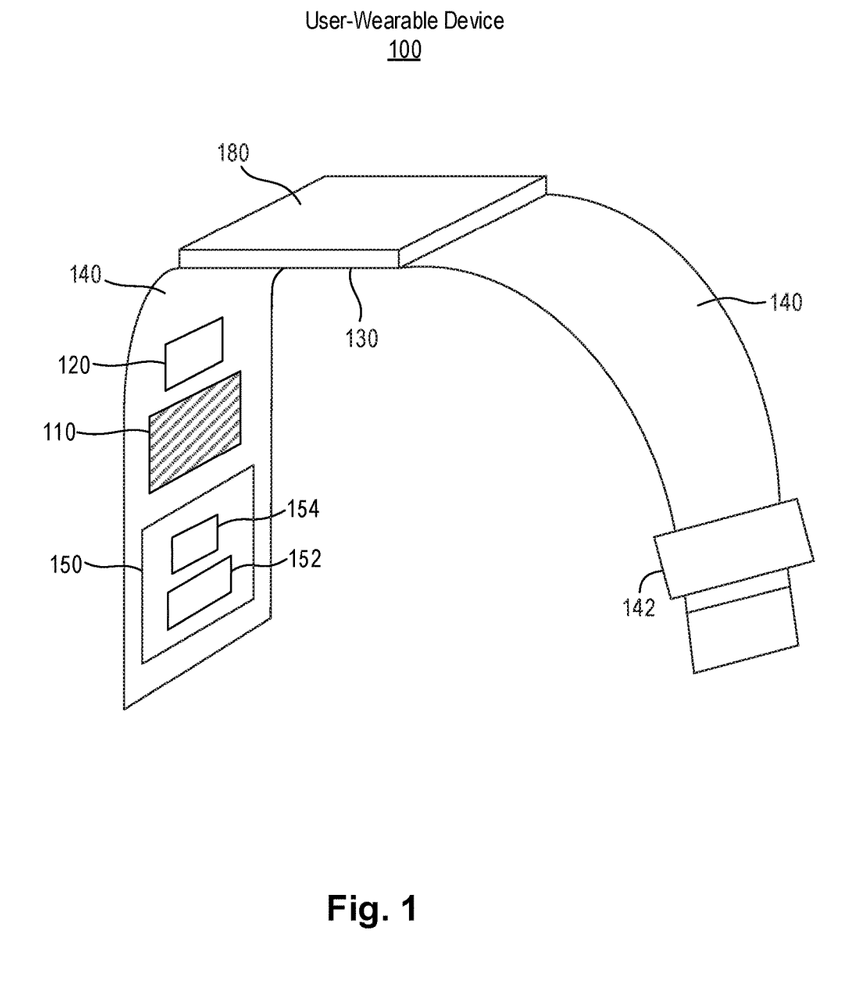
FIG. 1 illustrates an exemplary diagram of an electronic device according to one embodiment.

FIG. 1 illustrates an exemplary diagram of an electronic device according to one embodiment. Referring to FIG. 1, an electronic device, which may be the user-wearable device 100, has a display 180, a processor 130, a sensor module 150, an energy harvesting module 110, an energy storage module 120, a band 140, and a clasp 142. The band 140 may be wrapped around a wrist and the user-wearable device 100 may be held on the wrist by using the clasp 142. The sensor module 150 may include one or more sensors 152 and a local processor 154. The local processor 154 implements control function for the sensor module and may also perform processing or pre-processing of the sensed signals. The processor 130 implements control functions for the user-wearable device and may also perform further signal processing functions on the sensed signals. The local processor 154 or the processor 130 may also be referred to as a diagnostic processor. FIG. 1 illustrates an exemplary arrangement of the sensor module 150, the energy harvesting module 110, and the energy storage module 130 in the user-wearable device 100. The arrangement of elements shown in FIG. 1 is illustrative only and not intended to be limiting. In embodiments of the present disclosure, the wearable device 100 may be configured using other arrangement of elements. Specifically, the sensor module 150, the energy harvesting module 110, and the energy storage module 130 may be positioned in different locations of the wearable device. For example, the sensor module 150 may be located under the main body of the wearable device, opposite the display 180.

Although the user-wearable device 100 may be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smart phone, a laptop, or various medical devices at a hospital or a doctor's office.

The display 180 may output monitored physiological signals from the user's body for viewing by the user and/or others. The physiological signals being monitored may be referred to as biosignals or biometric data. The monitored biosignals may be, for example, heart (pulse) rate, pulse morphology (shape), pulse spacing (inter-beat intervals), respiration (breathing) rate, and blood pressure. The display 180 may also output instructions to the user or others in the use of the user-wearable device 100 or use of other measurement devices, as well as status and diagnostic results, for example.

The processor 130 may receive the monitored signals via a low-power sensor in the sensor module 150. In some examples, the sensor module 150 may include one or more sensors 152 that acquire signals from the user' when the user-wearable device 100 is worn by a user. The sensor 152 may be, for example, an accelerometer. The sensor module 150 may include the processor 154 for controlling the sensor 152, and also for processing the signals sensed by the sensor 152. For example, the processor 154 may decompose the signals monitored by the sensor 152, and then reconstruct the decomposed signals. Various embodiments of the disclosure may have the processor 130 also performing the functions of the processor 154. Various embodiments of the disclosure may also have different number of sensors.

In one example, the sensor 152 may be, for example, a motion sensor or an accelerometer that is used to continuously or near continuously monitor pulse related information. The sensor module 150 may include other sensors similar to the sensor 152 or a different type of sensor such as, for example, a thermometer for taking the user's temperature.

The energy harvesting module 110 collects energy from an ambient energy source where the harvested energy is applied to power the wearable device 100. In the present description, energy harvesting refers to the technique of capturing ambient energy, such as electromagnetic energy, solar energy, magnetic energy, kinetic energy, and thermal energy. The harvested energy may be stored in the energy storage module 120 and the energy storage module 120 provides the stored energy to power the user-wearable device 100. In some embodiments, the energy storage module 120 is a rechargeable battery or a capacitor.

Figure 2:
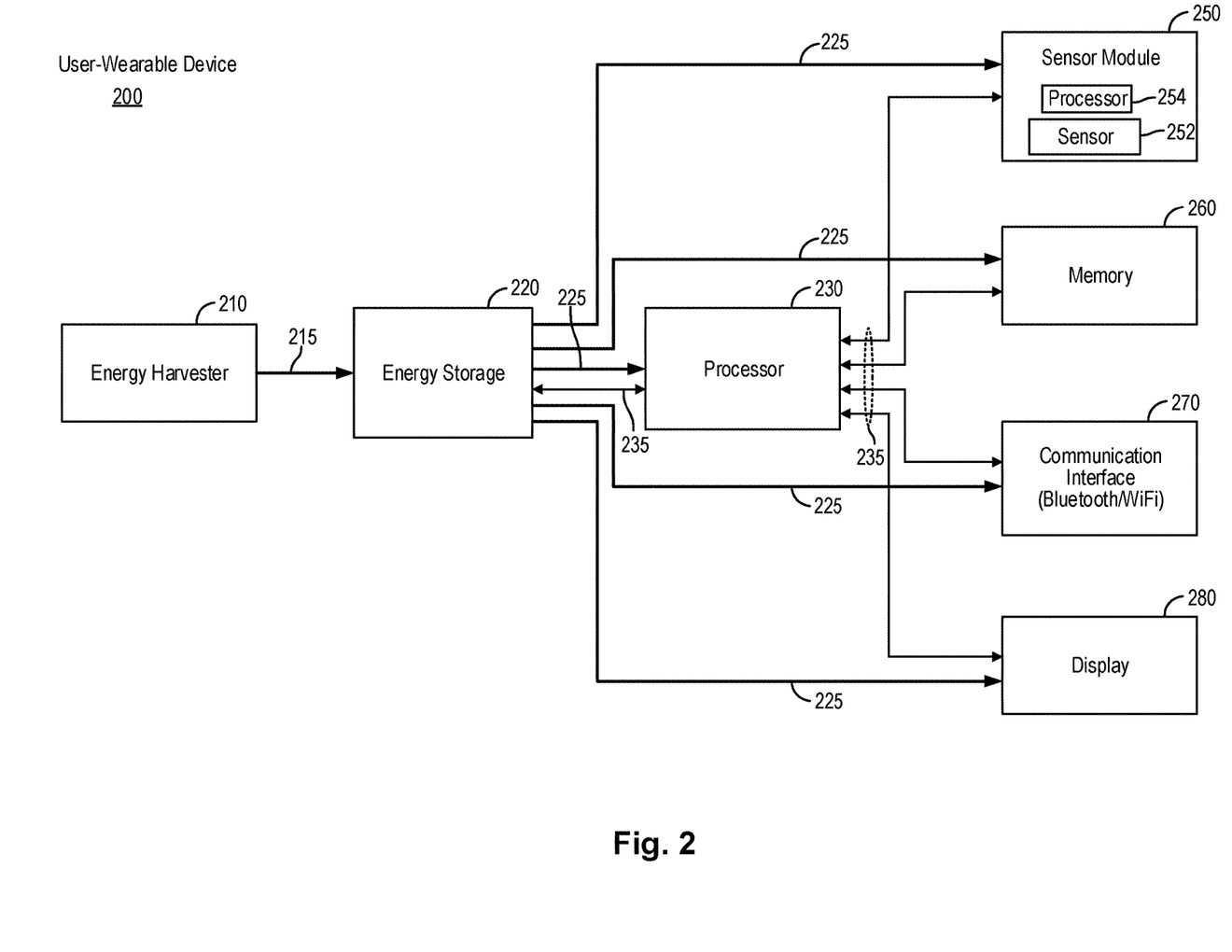
FIG. 2 illustrates a block diagram of an electronic device according to one embodiment.

FIG. 2 illustrates a block diagram of an electronic device according to one embodiment. Referring to FIG. 2, a user-wearable device 200 includes an energy harvesting module 210 (also referred to herein as an energy harvester) that continuously generates power by collecting energy from an ambient energy source. The harvested energy is provided through a power line 215 to be stored in an energy storage module 220. The energy stored in the energy storage module 220 is used to supply the remaining elements and circuitry of the user-wearable device 200, through power bus 225.

In the present embodiment, the user-wearable device 200 includes a processor 230 for controlling the sensing operation, the sampling schedule, the signal processing operation, and device communication events in the user-wearable device. In the present embodiment, the processor 230 is a low power processor. Further, in some embodiments, the processor 230 is a low power microcontroller (MCU). More specifically, the processor 230 communicates with the sensor module and other elements of the user-wearable device over a data bus 235. The processor 230 may provide control signals and may provide and receive data signals from the elements of the user-wearable device. For example, the processor 230 may communicate with the sensor module 250 over the data bus 235 to receive sensed signals and provide control signals. The processor 230 may further communicate with the energy storage module 220 over the data bus 135 to obtain stored energy level and other data.

The user-wearable device 200 includes a sensor module 250 including one or more biosignal sensors 252 to measure one or more biosignals of the user. In one embodiment, the biosignal sensor 252 is an accelerometer. Furthermore, in some embodiments, the sensor module 250 is implemented using ultra-low power sensors. In one exemplary embodiment, the sensor module 250 includes a tri-axial accelerometer that provides continuous heart rate, respiration rate, sleep, and cardiac arrhythmia monitoring that require less than 200 µA power supply in sensing mode. The sensor module 250 may be provided with a local processor 254 for controlling the sensor 252, and also for processing the biosignals sensed by the sensor 252. In some embodiments, the signal processing operation can be implemented at the local processor 254 and/or at the processor 230. Alternately, the local processor 254 may perform part of the signal processing, such as certain signal pre-processing, and the processor 230 implements signal processing methods for biometric determination. In embodiments of the present disclosure, the specific processor used to execute the biometric signal processing methods is not critical to the practice of the present disclosure.

Furthermore, in embodiments of the present disclosure, the wearable device 200 implements one or more biometric signal processing methods that are highly efficient and consume low level of power. The biometric signal processing methods can be implemented or executed in the local processor 254 of the sensor module 250 or in the processor 230. By using low power sensors and high efficient biometrics determining frameworks, the user-wearable device of the present disclosure system may be applied to continuously measure biometrics of a user as well as diagnose and screen individual health conditions where the user-wearable device is partially or completely powered by energy collected by the energy harvesting module.

In exemplary embodiments, the wearable device 200 implements one or more of the low power biometric sensing techniques and biometric inference and determination methods described in the following U.S. patent applications: U.S. patent application Ser. No. 14/931,440, entitled "Methods For Improving Response time, Robustness and User Comfort In Continuous Estimation Of Biophysiological Rates," by M. Wiggins et al., filed Nov. 3, 2015; U.S. patent application Ser. No. 14/928,072, entitled "Methods For Low-Power-Consumption, Robust Estimation Of Cardiovascular Periodicity, Contour Analysis, And Heart Rate," by Y. Li et al., filed Oct. 30, 2015; U.S. patent application Ser. No. 15/168,531, entitled "Methods And Apparatus For Heart Rate And Respiration Rate Estimation Using Low Power Sensor," by Y. Li et al., filed May 31, 2016; U.S. patent application Ser. No. 15/264,333, entitled "System And Method For Providing A Real-Time Signal Segmentation And Fiducial Points Alignment Framework," by Y. Li, filed Sep. 13, 2016; U.S. patent application Ser. No. 15/370,468, entitled "System And Method For Snoring Detection Using Low Power Motion Sensor," by Y. Li et al., filed Dec. 6, 2016; U.S. patent application Ser. No. 15/726,827, entitled "System And Method For Continuous Background Heartrate And Heartbeat Events Detection Using A Motion Sensor," by Y. Li, filed Oct. 6, 2017; U.S. patent application Ser. No. 15/726,756, entitled "System And Method For Real-Time Heartbeat Events Detection Using Low-Power Motion Sensor," by Y. Li, filed Oct. 6, 2017. The aforementioned patent applications are incorporated by reference herein.

The user-wearable device 200 includes other elements to support the functioning of the device. In the present embodiment, the user-wearable includes a display 280 for displaying biometric or receiving user input, a memory 260 for storing operation instruction codes and/or raw or processed signals and/or other data, and a communication interface 270 to facilitate communication with an external device, such as a smart phone. The display 280 may also include input devices (not shown) such as, for example, buttons, dials, touch sensitive screen, and microphone. While the user-wearable device 200 is described as including these various element, other embodiments may use other architectures where the different functionalities are grouped differently. For example, the grouping may be in different integrated circuit chips. Or the grouping may be combining different elements such as the communication interface 270 and the processor 230 together. In the present embodiment, the energy storage 220, the display 280, the memory 260 and the communication interface 270 communicates with the processor 230 over the data bus 235.

The processor 230 may control operation of the sensor module 250 as well as receive monitored signals from the sensor module 250. The processor 230 may control the user-wearable device 200, including processing the monitored signals from the sensor module 250, displaying the processed signals on the display 280, receiving input from the display 280, interfacing with various devices via the communication interface 270 by executing instructions in the memory 260. The operating system and applications may be stored in the memory 260. Other embodiments of the present disclosure may use different memory architectures that are design and or implementation dependent. The communication interface 270 may allow the user-wearable device 200 to communicate with other devices via, for example, a wired or wireless protocol such as Universal Serial Bus (USB), Bluetooth, Near Field Communication (NFC), and Wi-Fi.

The processor 230 may operate using different architectures in different embodiments. For example, the processor 230 may use the memory 260 to store instructions to execute, or the processor 230 may have its own memory (not shown) for its instructions. Although in the present embodiments, the device 200 has separate processors 230 and 254, the various embodiments need not be limited so. There may be one processor 230 that controls the functionality of the user-wearable device 200, or there may be multiple processors for the user-wearable device 200.

Energy Harvester

In embodiments of the present disclosure, the energy harvesting module 210 may be implemented using energy harvesting technology suitable for wearable devices, currently available or to be developed. In one embodiment, the energy harvesting module 210 is implemented as a thermoelectric generator integrated into the wearable device, such as on the wristband. The thermoelectric generator operates to measure the temperature difference between a body temperature of the user and the environment external to the user and to generate a voltage proportional to the temperature difference. In other words, the thermoelectric generator captures the thermal flux of heat from the user's body relative to the ambient space and converts the thermal flux into power, for example using the Peltier effect. In a thermoelectric generator, higher temperature gradients lead to higher energy generation.

In an alternate embodiment, the energy harvesting module 210 is implemented as a kinetic energy harvester arranged to capture energy generated by body movements and to convert the captured kinetic energy into power for powering the wearable device. In yet another embodiment, the energy harvesting module 210 is implemented as a radio frequency (RF) energy harvester arranged to capture environmental RF signals such as radio and television broadcasting signals and convert the captured RF energy into power for powering the wearable device.

In other embodiments, the energy harvesting module can be implemented using other types of energy harvesting technology, such as a piezoelectric energy generator, a solar power generator, an ambient vibration-powered energy harvester, a photovoltaic energy generator, and an electrodynamic power generator. Other techniques can be used for energy harvesting without deviating from the scope of the present disclosure. With advances in material science as well as miniaturization of hardware, more energy harvesting options that are suitable for wearable devices will become available.

In embodiments of the present disclosure, the harvested energy is stored in the energy storage module 220 and then distributed to the other elements of the wearable device. The energy storage module may be implemented using various types of energy storage, including but not limit to, chemical storage elements (such as rechargeable batteries), electrical storage elements (such as capacitors or super-capacitors), and mechanical storage elements (such as springs or flywheels).

Accordingly, in some embodiments, the harvested energy is stored on a capacitor as the energy storage module 220. In alternate embodiments, the harvested energy is used to charge a built-in rechargeable battery as the energy storage module 220.

In the present description, the terms "energy" and "power" are sometimes used interchangeably to refer to the electrical energy being generated and consumed by the user-wearable device. It is understood that "energy" refers to the total amount of work done while "power" refers to how fast the work can be done. Electrical energy is often measured in watt-hour. Power is defined as the rate of producing or consuming energy and is measured in watt. In other words, power is energy per unit of time. For example, one watt of electrical power, maintained for one hour, equals one watt-hour of energy. It is understood that although the terms "energy" and "power" may be used interchangeably in the present description, these terms retain their respective ordinary meanings in the arts.

Biometrics Measurement

In embodiments of the present disclosure, the sensor module 250 is implemented using an ultra-low powered microelectromechanical (MEMS) sensors such are an accelerometer or a gyroscope. The MEMS sensor is applied to capture body movements and vibration information such as activity, cardiac indicators (e.g., heart rate, heart rate variability (HRV), and cardiac arrhythmia), respiratory information, sleep information and snoring events.

In another embodiment, an electrocardiogram (ECG) sensor may be implemented in a wrist-based wearable device where ECG measurement is triggered once the ECG lead is touched by a user. Alternately, the ECG sensor may be implemented as a chest-worn patch device where the ECG measurement will be collected continuously.

In some embodiment, an optical photoplethysmogram (PPG) sensor is implemented in the user-wearable device. Current PPG sensors tend to operate with considerably high power consumption. Aggressive power management mechanism may be applied to enable the use of PPG sensors in the user-wearable device with long operating time. However, PPG sensors may become more efficient in future development, making PPG sensors suitable for self-powered wearable devices.

Finally, in alternate embodiments, sensors such as a bioimpedance sensor, a galvanic skin response (GSR) sensor, a piezoelectric sensor, and a strain gauge sensor may be applied for biometrics measurement with power optimization.

Power Optimization

In embodiments of the present disclosure, the processor 230 of the user-wearable device 200 is configured to implement power optimization methods. In one embodiment, the processor 230 incorporates an adaptive power control module, which can be implemented in software or firmware or both, to implement a power management scheme to realize a power balance operation between the power generated by the energy harvesting module and the power consumed by the sensor module and the processor module. More specifically, in one embodiment, the adaptive power control module is configured to adaptively adjust the sensing duty cycle and the signal processing run schedule based on user needs while balancing the energy generation versus consumption.

In one embodiment, the user-wearable device 200 includes the energy harvesting module 210 capable of generating N watts of power at room temperature. The sensor, such as the accelerometer, and the processor 230 consumes power of $P_{sleep}$ in an inactive or sleep mode and a power of $P_{sense}$ at a high-resolution biosignal sampling mode (also referred to as the "sensing mode"), and the processor 230 consumes a power of $P_{process}$ during signal processing run time during the sensing mode. Accordingly, a power generating-consuming balance equation is as follows:

$$E_{EH}+E_{stored} \geq \int_{t_1}^{t_2}((P_{sense}+P_{process}) \cdot \theta + P_{sleep} \cdot (1-\theta))dt \quad (1)$$

where $\theta$ is a duty cycle of sensing mode and $(1-\theta)$ is the time period for the sleep mode, $E_{EH}$ is power generated in a given time duration, and $E_{stored}$ is the initial energy stored in the energy storage module. More specifically, duty cycle $\theta$ refers to the percentage of time within a given duration when the sensing mode is activated. In embodiments of the present disclosure, the user-wearable device is operated in one of two modes—the sensing mode where active sensing and signal processing is being performed and the sleep or inactive mode where no sensing or signal processing is carried out. The sensing mode is activated for the duty cycle—that is a given percentage of time within a given duration—and the sleep mode is activated for the remaining time outside of the duty cycle during the same given duration.

Equation (1) is the power balance equation which describes the condition to achieve a power balance between energy harvesting and sensing/signal processing to realize a self-charging or battery-less wearable device. In one embodiment, the duty cycle $\theta$ is adjusted to set the power consumption so as to achieve the desired power balance in Equation (1). More specifically, as described by Equation (1), over a time period between time $t_1$ to $t_2$, the sum of the energy generated by the energy harvester $E_{EH}$ and the energy stored in the energy storage module $E_{stored}$ is equal to or greater than the sum of the energy consumed by the sensor module for performing sensing operation during a first duty cycle and by the processor module for performing signal processing during the first duty cycle $((P_{sense}+P_{process}) \cdot \theta)$ and the energy consumed by the sensor module and the processor module during an inactive mode outside of the first duty cycle $(P_{sleep} \cdot (1-\theta))$.

In embodiments of the present disclosure, to achieve the power balancing, the duty cycle for the sensing mode is adjusted so as to set the desired level of power consumption for the amount of energy being generated. For example, the duty cycle $\theta$ can be reduced to reduce the time spent on sampling and increase the time in sleep mode so as to conserve energy. In one example, sampling is reduced during non-critical situations, such as high activity level of the user and sampling is increased during low activity period of the user, such as when the user is resting or is asleep.

By applying adaptive power control to maintain the power balance relationship of Equation (1), the user-wearable device 200 may achieve self-powering or the device charging frequency may be significantly reduced. In particular, in some embodiments, when the power balance Equation (1) above can be maintained valid for all time duration, that is, the energy harvester generates more power than device consumption, the user-wearable device can be operated in the continuous sensing mode with the sensing duty cycle set to 1 ($\theta$=1) or with 100% duty cycle. That is, the sensing mode is operating 100% of the time. Otherwise, the sensing duty cycle θ should be set according to power consumption ratio between sensing mode and the inactive mode. In one example, the user-wearable device operates in a high resolution sensing mode for 20% of the time (θ=0.2) and in a low power mode for 80% of the time (θ=0.8).

In particular, Equation (1) has to be satisfied if the present device operates continuously for time period $t_1$-$t_2$. In some embodiments, a system efficiency factor μ can be defined as the power ratio of sensing mode and the signal processing mode. That is, the system efficiency factor can be given as:

$$\mu = \frac{P_{sense}}{P_{process}},$$

where a large system efficiency factor μ indicates high system efficiency. In some cases, the power consumed by the sensor module, $P_{sense}$, can be set as a constant value when a particular sensor has been selected. In other embodiments, the power consumed by the signal processing operations, $P_{process}$, may be fixed, such as when the wearable device system configuration is established. In that case, the system efficiency factor μ can be used as a benchmark for selecting the desired sensor to achieve the desired system efficiency.

Furthermore, harvested power depends heavily on factors such as ambient temperature and a user's energy expenditure. In the case of a thermoelectric generator, low user activity (such as a user sleeping) and warm ambient temperatures both generate less power whereas high user activity (such as a user exercising) or low ambient temperature outputs more power. In some embodiments, the user-wearable device of the present disclosure may be configured to quantify user energy expenditure and activity level based on the energy harvesting output level.

In some embodiments, the user-wearable device of the present disclosure may be used for diagnosing or screening of health conditions, where the user-wearable device adjusts the sensing scheduling according to user needs. For example, in the case the user-wearable device is used for sleep apnea monitoring/diagnosing, the sensing mode is triggered when the device detects that the user is sleeping or when suspicious events are identified. Regular background monitoring such as daytime heart rate and respiration rate are be scheduled according to power balance Equation (1).

In some cases, in order to maintain the power balance equation above, high power consumption biosignal sensors, such as a continuous PPG sensor should be precluded from the sensor module of the user-wearable device. Also, complicated computations, such as complex neural network, should be avoided in order to minimize the processor wake-up periods.

Figure 3:
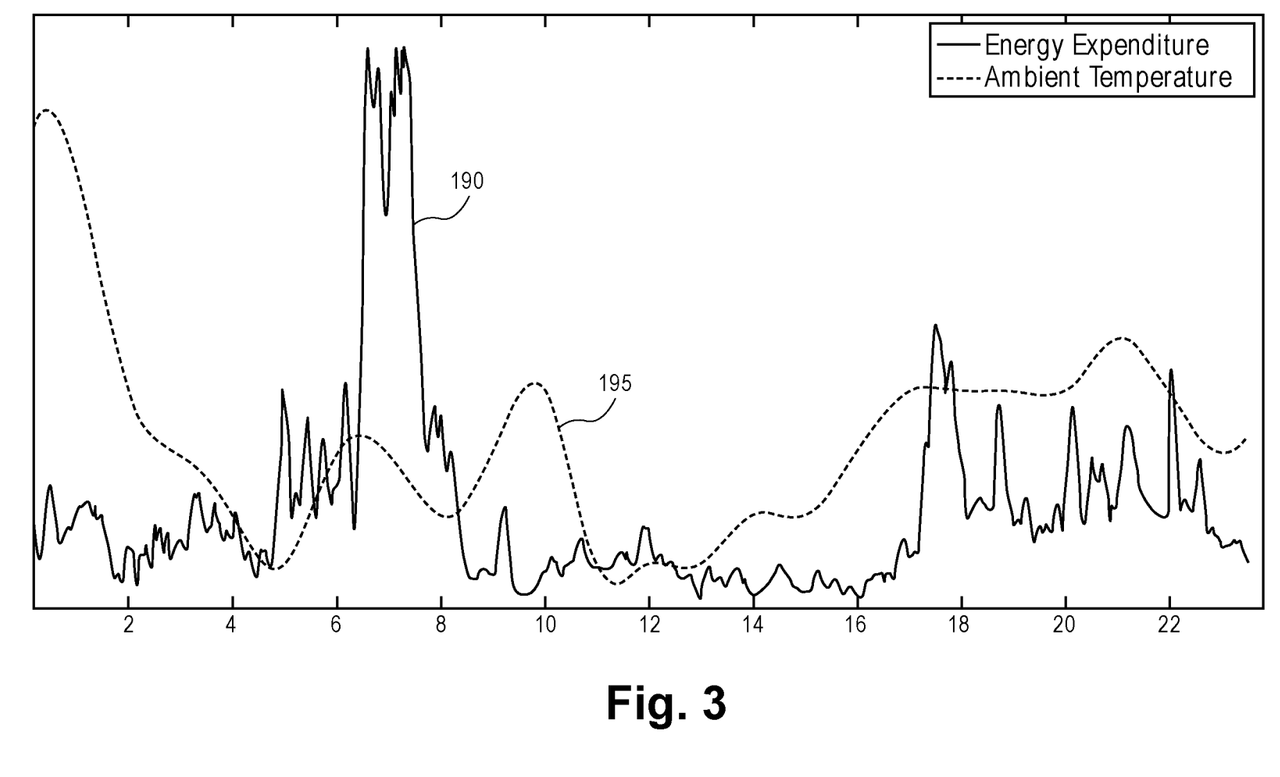
FIG. 3 illustrates an exemplary waveform of a user's 24-hour energy expenditure and ambient temperature change.

In further embodiments, the user-wearable device implements a regression model to maximize energy utilization. FIG. 3 illustrates an exemplary waveform of a user's 24-hour energy expenditure (curve 190) and ambient temperature change (curve 195). By quantifying subject's historical lifestyle pattern (energy expenditure pattern) as well as historical temperature data, such factors may be applied into a predictive regression model that outputs optimal power scheduling. In one embodiment, when the user-wearable device is initialized, an embedded model is set to a default setting. After the device learns the user's individual usage pattern, the embedded model gradually regresses to an optimal setting. That is, the power schedule for the user-wearable device is individualized for each user based on the user's activity pattern or the user's energy expenditure.

In some embodiments, the user-wearable device implements a predictive model to analyze the current energy harvesting output and to predict the energy generation trend. Based on the predicted energy generation trend, the predictive model determines the duty cycle to use. For example, in the event that the current energy harvesting level is too low, the prediction model reduces the duty cycle to conserve energy in anticipation of reduced harvested energy in the future.

In embodiments of the present disclosure, a self-powered wearable device contains a tri-axial accelerometer and an ECG sensor in the sensor module. The tri-axial accelerometer continuously samples the user's body vibration and further ballistocardiogram (BCG) or seismocardiogram (SCG) and respiratory signal can be extracted from raw motion signal. Background resting heart rate and respiration rate may be derived from extracted biosignals. Moreover, the derived heart rate and respiration rate outputs combined with raw motion signals can further derive biometrics such as energy expenditure, steps, snoring, sleep quality, sleep apnea, HRV and user's mood (stress or emotion).

In embodiments of the present disclosure, the user-wearable device can be configured as a self-powered atrial fibrillation screening device which includes an accelerometer that detects irregular cardiac rhythm and abnormal heart beat morphology. When abnormal events are detected, the user-wearable device is configured to trigger an ECG measurement event and notifies the user for a data collection request. The ECG raw signal may be either processed by the user-wearable device or stored for further diagnosis.

In some embodiments, the user-wearable device may provide measurement locations on one or more body locations or even remote locations. Such locations include, but are not limited to, a wrist, a chest patch, an earphone, and a shoe. For example, the present system includes a wrist-based smartwatch or chest worn patch using a thermoelectric generator. In another example, a kinetic or piezoelectric powered device with an ultra-low power motion sensor can be embedded into shoes to monitor daily activity as well as BCG related applications.

According to one embodiment, the present system includes a wearable device for biometric measurement or diagnosing/screening for health conditions where the sum of power consumed by sensing operations and signal processing operations is partially or completely powered by the energy harvesting module. The wearable device includes a low power sensor includes at least one or more of, but is not limited to, a PPG sensor, a MEMS sensor, an ECG sensor, a bioimpedance sensor, a GSR sensor, and a piezoelectric sensor, and where the biometrics extraction includes one or more of, but is not limited to, PPG, ECG, BCG, and SCG.

The user-wearable device of the present disclosure may include an adaptive power control module that adjusts sensing duty cycle/schedule and process time based on user setting and power generating-consuming balance. In some embodiments, the user-wearable device of the present disclosure includes predictive models that are used to adjust sensing duty cycle and schedule based on user need and projected energy harvesting. The device adjusts a sensing sampling frequency based on user needs and power balance. The device adjusts the balance between sensor operation and duty cycle and sensor and processing activation based on the power produced by the energy harvesting system, while the device incorporates low power sensing modalities including PPG, ECG, BCG, and SCG; and where the device extracts biometrics including, but are not limited to, heart rate, heart rate variability, arrhythmia detection, activity level, sleep, snoring, and respiration.

According to one embodiment, the user-wearable device is implemented as a sleep apnea detection and/or screening device that provides power generation-consumption balancing; and contains sensors including an accelerometer (e.g., a movement, BCG, SCG, position, and declination), a pulse oximeter, and sensor processing components for heart rate, heart rate variability, respiration, snoring detection, SpO2, sleep onset offset, sleep duration/efficiency, sleep position, and apnea event detection.

According to one embodiment, the user-wearable device is implemented as an arrhythmia detection and/or screening device that provides power generation-consumption balancing; and contains sensors including an accelerometer (e.g., movement, BCG, SCG, position, and declination), an ECG circuit, and sensor processing components for heart rate, heart rate variability, activity level, sleep, arrhythmia detection, stroke volume, cardiac output, and reduced peripheral perfusion.

According to one embodiment, the user-wearable device is implemented as a wearable device for biometric measurement having an energy harvesting component, and one or more low power inertial measurement sensors with associated power optimized biometric inference methods including a resting heart rate, a respiration rate, steps, activity/energy expenditure, sleep monitoring, and snoring detection; where the sum of power consumed by the sensing processes is partially or completely powered by energy harvesting component. The wearable device further includes an adaptive power control module configured to adjust a sensing duty cycle schedule and signal process time based on a user setting and power generating/consuming balance as described in Equation (1).

According to one embodiment, the user-wearable device for biometric measurement includes an energy harvesting component, and one or more of a PPG sensor, a MEMS sensor, an ECG, a bioimpedence sensor; a GSR, and a piezoelectric sensor; and where the balance of power consumed by sensing processes is partially or completely powered by energy harvesting component, controlled by an adaptive power control module configured to adjust a sensing duty cycle schedule and signal process time based on a user setting and power generating/consuming balance as described in Equation (1).

Figure 4:
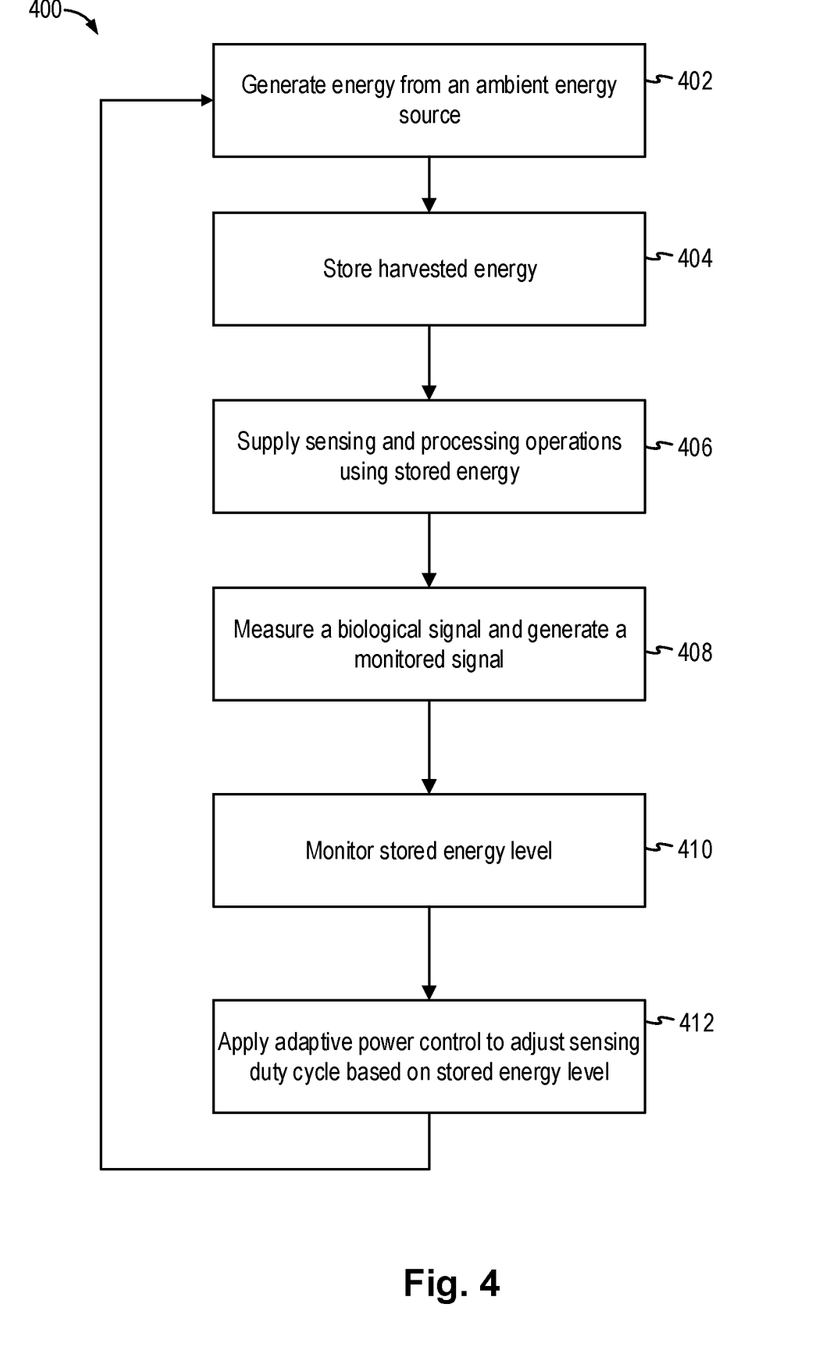
FIG. 4 illustrates a flowchart of a method for biometric measurement in a user-wearable device in one embodiment.

FIG. 4 illustrates a flowchart of a method for biometric measurement in a user-wearable device in one embodiment. Referring to FIG. 4, a method 400 for biometric measurement includes generating energy from an ambient energy source (at 402) and storing the harvested energy (at 404). For example, the energy can be harvested by an energy harvesting module and stored in an energy storage module. The method 400 supplies the biometric sensing operation and the signal processing operation using the stored energy (at 406). The method 400 senses at least one biological signal during the sensing operation and generates at least one monitor signal during the signal processing operation from the sensed signal (at 408). The sensed signal may be a motion signal. The monitored signal may be, for example, heart (pulse) rate, pulse morphology (shape), pulse spacing (inter-beat intervals), respiration (breathing) rate, and blood pressure.

The method 400 monitors the stored energy level (at 410). The method 400 further applies adaptive power control to adjust the sensing duty cycle in response to the stored energy level (at 412). In other words, when the stored energy level is low, the sensing duty cycle may be reduced to conserve power. In some embodiments, the method 400 applies the adaptive power control to adjust the processing time of the signal processing operation in response to the stored energy level. In other words, when the stored energy level is low, the processing time may be reduced to conserve power. The method 400 repeats to generate energy from the ambient energy source (at 402).

The above detailed descriptions are provided to illustrate specific embodiments of the present disclosure and are not intended to be limiting. Numerous modifications and variations within the scope of the present disclosure are possible. The present disclosure is defined by the appended claims.

What is claimed is:

1. A user-wearable device for biometric measurement of a user, comprising:
an energy harvester;
an energy storage coupled to the energy harvester to store energy harvested by the energy harvester; and
components configured to consume the energy stored in the energy storage, the components including:
a sensor configured to measure at least one biological signal of the user, the sensor configured to receive power from the energy storage; and
a processor configured to process the biological signal measured by the sensor, the processor configured to receive power from the energy storage,
wherein the sensor and the processor are configured to be controlled by an adaptive power controller that is configured to adjust a sensing duty cycle schedule of the sensor and a signal process time of the processor based on an energy expenditure pattern of the user and an activity level of the user to realize power balance between the energy generation by the energy harvester and energy consumption by the components configured to consume the energy stored in the energy storage.

2. The user-wearable device of claim 1, wherein the sensor is selected from one of a low power inertial measurement sensor, a photoplethysmogram (PPG) sensor, a microelectromechanical systems (MEMS) sensor, an electrocardiogram (ECG) sensor, a bioimpedance sensor, a galvanic skin response (GSR) sensor, and a piezoelectric sensor.

3. The user-wearable device of claim 2, wherein the sensor in the sensor is configured to measure at least one biological signal of the user, and wherein the biological signal is selected from resting heart rate, respiration rate, activity energy expenditure, sleep monitoring, and snoring detection.

4. The user-wearable device of claim 2, wherein the low power inertial measurement sensor comprises an accelerometer.

5. The user-wearable device of claim 1, wherein the adaptive power controller is configured to adjust the sensing duty cycle schedule and the signal process time so that the power consumed by the sensing operation of the sensor and the signal processing operation of the processor is equal to or less than the power generated by the energy harvester.

6. The user-wearable device of claim 1, wherein the adaptive power controller is configured to adjust the sensing duty cycle schedule and the signal process time so that, over a first time period, the sum of the energy harvested by the energy harvester and the energy stored in the energy storage is equal to or greater than the sum of the energy consumed by performing the sensing operation and the signal processing operation during a first duty cycle and the energy consumed during an inactive mode outside of the first duty cycle.

7. The user-wearable device of claim 1, wherein the energy harvester comprises a thermoelectric generator arranged to measure the temperature difference between a body temperature of the user and the environment external to the user and to generate a voltage proportional to the temperature difference.

8. The user-wearable device of claim 1, wherein the energy harvester comprises one of a kinetic energy harvester, radio frequency (RF) energy harvester, piezoelectric energy generator, solar power generator, ambient vibration-powered energy harvester, photovoltaic energy generator, and electrodynamic power generator.

9. The user-wearable device of claim 1, wherein the energy storage comprises a rechargeable battery or a capacitor.

10. The user-wearable device of claim 1, wherein the power consumed by the sensor operation and the signal processing operation is supplied by the energy harvester only.

11. The user-wearable device of claim 1, wherein the components include a plurality of sensors, and the adaptive power controller selects the sensor from the plurality of sensors to realize power balance between the energy generation and the energy consumption.

12. The user-wearable device of claim 1, wherein the user-wearable device includes the adaptive power controller.

* * * * *